United States Patent
Brown

[11] Patent Number: 6,095,157
[45] Date of Patent: Aug. 1, 2000

[54] TOOTHBRUSH WITH A DETACHABLE AND DISPOSABLE BRISTLE HEAD AND ATTACHED FLOSS DISPENSING UNIT

[76] Inventor: Polly Brown, 5391 Robertson Path, Lithonia, Ga. 30038

[21] Appl. No.: 09/277,083

[22] Filed: Mar. 26, 1999

[51] Int. Cl.[7] .................................................. A45D 44/18
[52] U.S. Cl. ............................................. 132/309; 132/311
[58] Field of Search ....................... 132/308, 309, 132/311, 321, 323, 324, 325; 401/268, 123, 124, 125; 15/167.1

[56] References Cited

U.S. PATENT DOCUMENTS

| | | | |
|---|---|---|---|
| 3,850,182 | 11/1974 | Clark, Jr. | 132/309 |
| 4,821,752 | 4/1989 | Widlak | 132/309 |
| 4,887,621 | 12/1989 | Vallieres | 132/309 |
| 5,348,028 | 9/1994 | Gustavel | 132/309 |
| 5,676,167 | 10/1997 | Garner | 132/309 |
| 5,865,195 | 2/1999 | Carter | 132/309 |

Primary Examiner—Gene Mancene
Assistant Examiner—Pedro Philogene

[57] ABSTRACT

A toothbrush and apparatus includes a detachable bristle head and an attached dental floss dispenser assembly supported by a handle with both devices at the same end of the handle. The dental floss assembly is affixed to the back of the detachable bristle head and both screw into the hollow housing at the same end of the handle. Both the detachable bristle head and attached dental floss device are circular in structure with a sunken hole at the rear base of the housing to allow dispensing of the floss. A floss cutting metal hook is located mid-distance along the frontal base of the support handle.

1 Claim, 4 Drawing Sheets

TOOTHBRUSH WITH A DETACHABLE AND DISPOSABLE BRISTLE HEAD AND ATTACHED FLOSS DISPENSING UNIT

BACKGROUND OF THE INVENTION

1. Field of the Invention

The invention relates to toothbrushes wherein the detachable and disposable bristle head has affixed to it a floss dispensing device with a given quantity of floss contained therein.

Because proper dental care is often neglected in situations where meals are not eaten at home or where carrying a complete set of dental hygienic accessories proves burdensome, many aliments in oral hygiene occur.

Basic to oral hygiene is the practice of brushing and flossing after each meal. Therefore, the invention further relates to an improved toothbrush with a detachable and disposable bristle head and floss dispensing device which meets this dental hygienic need through a convenient, unitary in construction toothbrush which is easily transportable. It results in proper and immediate dental hygienic care for those who might otherwise delay the procedure of brushing and flossing until they reach their homes or omit the procedure altogether.

2. Description of the Prior Art

Various prior art toothbrush and floss apparatus and the method of their construction are known and are found to be exemplary of the U.S. prior art. They are:

| U.S. Pat. No. | Inventor |
| --- | --- |
| 4,016,891 | Kupperman, et.al. |
| 4,887,621 | Vallieres |
| 5,676,167 | Garner |

The Kupperman patent is an assembly which includes a dental floss holder on the toothbrush handle and the like for supporting a strip of floss in taut condition ready for use.

The Vallieres patent is an assembly which includes a hollow handled toothbrush with a detachable toothbrush and a cavity for receiving a spool of dental floss on a support platform used for loading and unloading the floss. The platform includes a opening for the dental floss and supports a cutter which is protected by removable screw cap covers.

The Garner patent is an assembly which includes a toothbrush supported by a handle which includes a brush end and a floss-supporting end which includes housing with a hinged cap allowing access to the dental floss.

These patents, or known prior uses, disclose various types of combination toothbrush and dental floss assemblies, but none of them, either singularly or collectively, disclose the specific details as to bear upon the claims of the present invention.

SUMMARY OF THE INVENTION

An object, advantage, and feature of the present invention is to provide a novel disposable combination toothbrush and dental floss which is both efficient in use and inexpensive thereby permitting the user to conveniently utilize the same when and wherever practical.

Another object of the present invention is to provide a disposable toothbrush head for easy replacement once it is worn.

Another object of the present invention is to provide a supply of dental floss which is easily accessible and discarded after use and replaceable once depleted.

A further object of the present invention is eliminate the need for the user to replace the entire toothbrush handle when replacing the toothbrush head and floss.

Furthermore, another object of the present invention is to provide a toothbrush and floss device which is easily transportable and available for use in most social situations and occasions.

DESCRIPTION OF TIE SEVERAL VIEWS OF THE DRAWINGS

DESCRIPTION OF THE PREFERRED EMBODIMENT OF THE INVENTION

Figure 1:
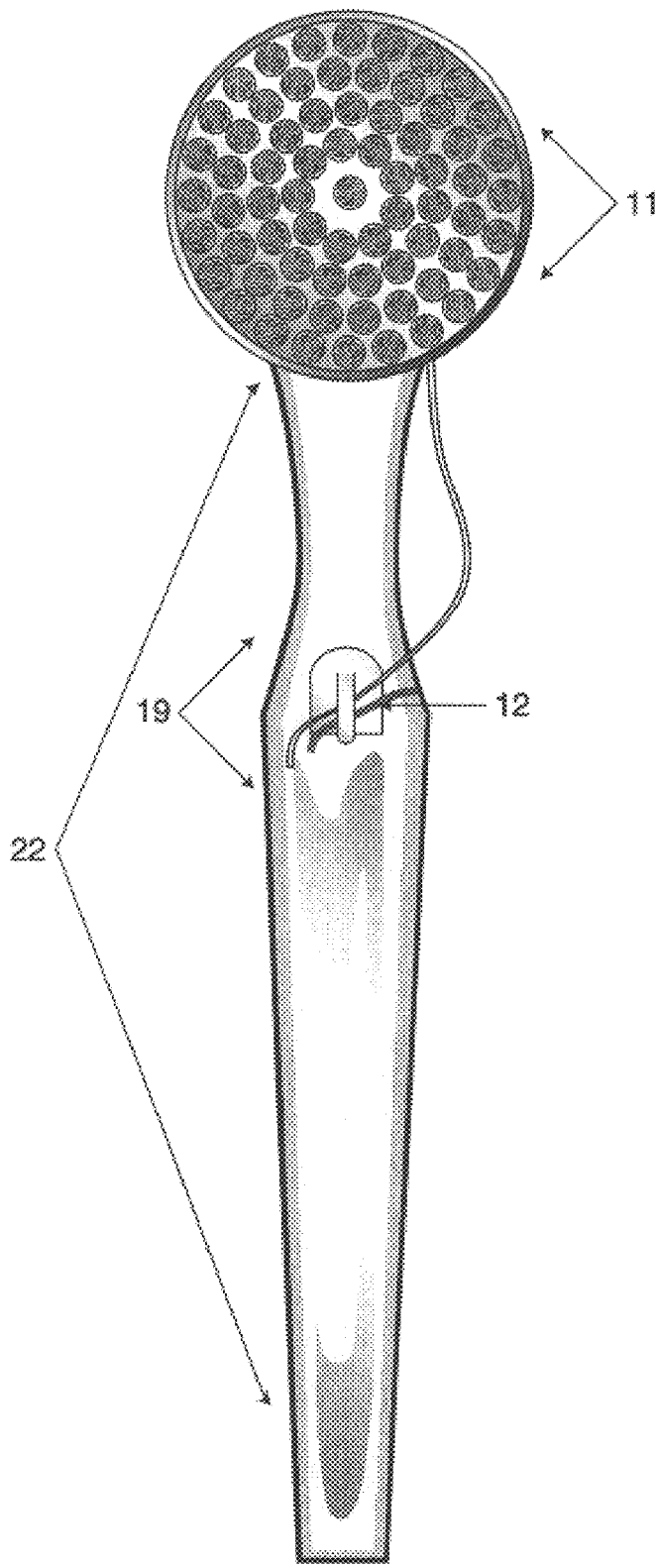
FIG. 1 is a frontal view of the device illustrating the circular shape of the bristle head and the dental floss metal cutting device at the mid-point of the supporting handle.
Figure 2:
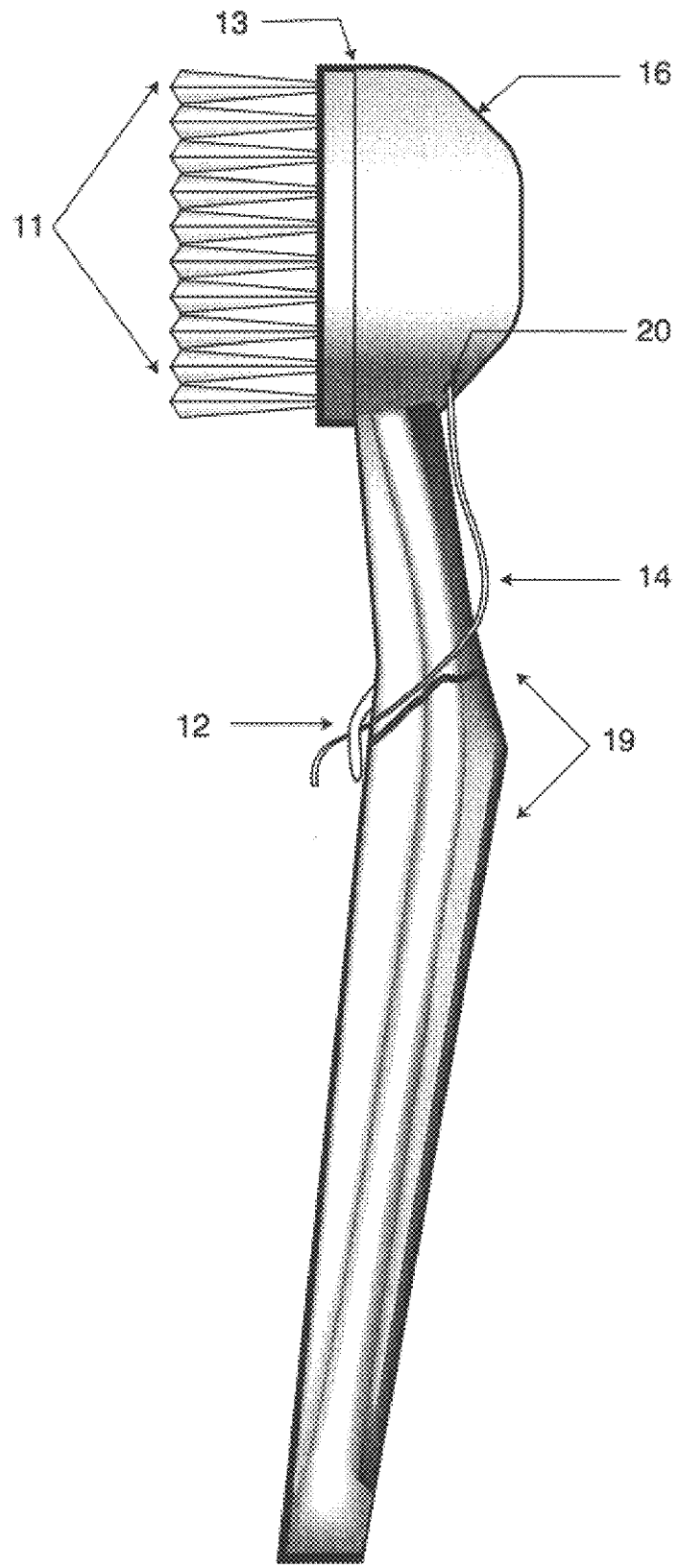
FIG. 2 is a side view of the device illustrating the detachable and disposable bristle head and floss dispensing unit in the secure or screwed position with a portion of the floss exposed through the sunken hole at the rear of the housing unit and positioned for cutting by the cutting device.

Referring now to the drawings, there is shown in FIG. 1. the Toothbrush with the Detachable and Disposable Bristle Head and Affixed Floss Dispensing Unit, hereafter referred to as the device 22, which comprises a circular bristle head 11 mounted on longitudinal support handle 19 with a metal cutting hook 12. FIG. 2 shows the detachable and disposable circular bristle head 11 in a secure or screwed position 13, into the housing unit 16, with floss in dispensed position 14, through the sunken hole 20 at the rear of the housing unit 16, and positioned for cutting by the metal cutting device 12 on the frontal base of the supporting handle 19.

Figure 3:
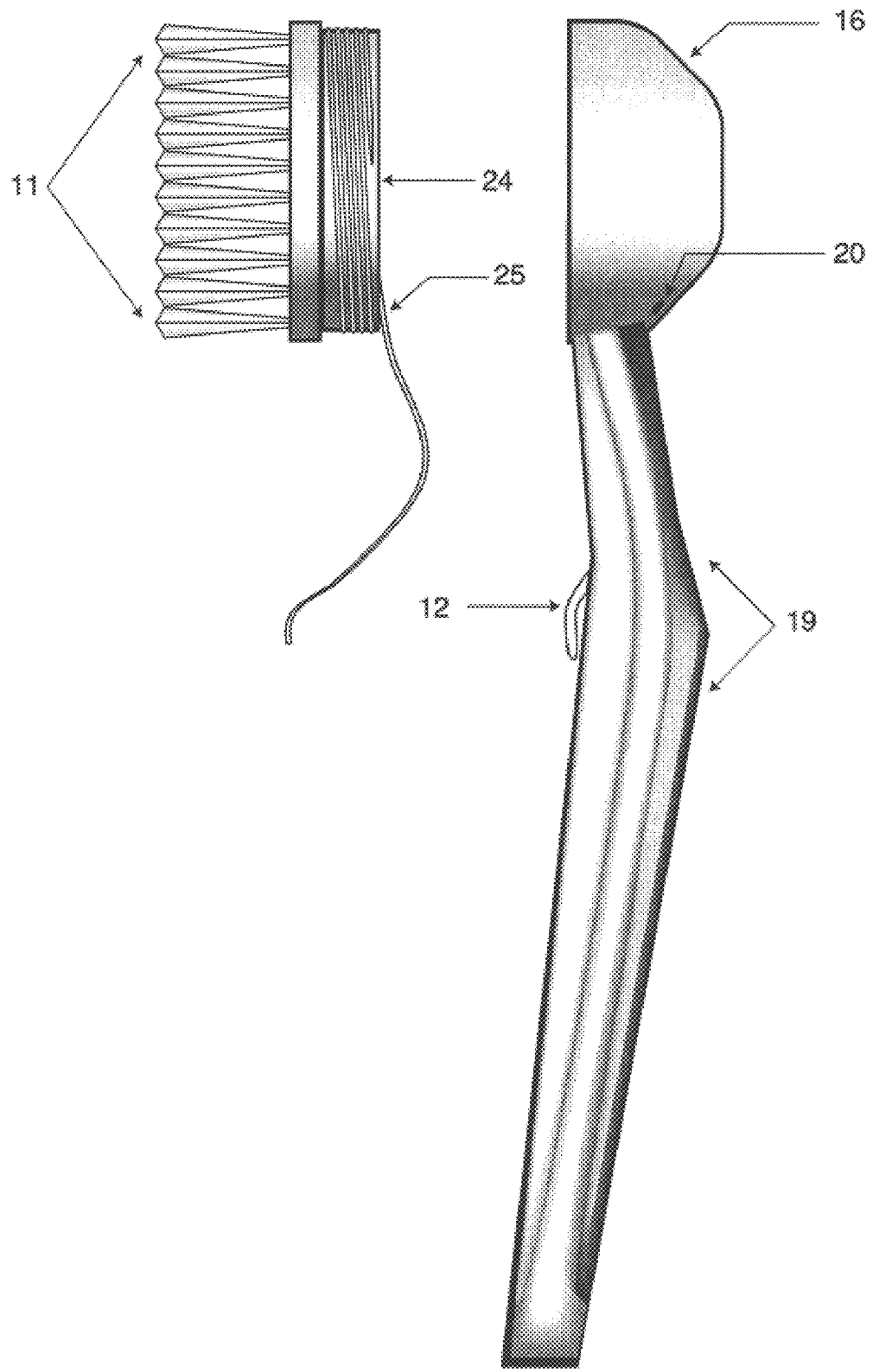
FIG. 3 is a side view of the device illustrating the detachable and disposable bristle head and attached floss dispensing unit in the unsecured or unscrewed position. Further illustrated is the retainable and reusable support handle containing the sunken hole for easy dispensing of the floss and the floss cutting device at the mid-point of handle.

FIG. 3 shows the detachable and disposable circular bristle head 11, and encased floss dispensing unit 24 containing floss 25 in the unsecured or unscrewed position from the housing unit 16 with the sunken hole 20, at the top end of the support handle 19 for dispensing the floss 25, which will be cut by the metal cutting device 12 on the front base of the support handle 19.

Figures 4, 5:
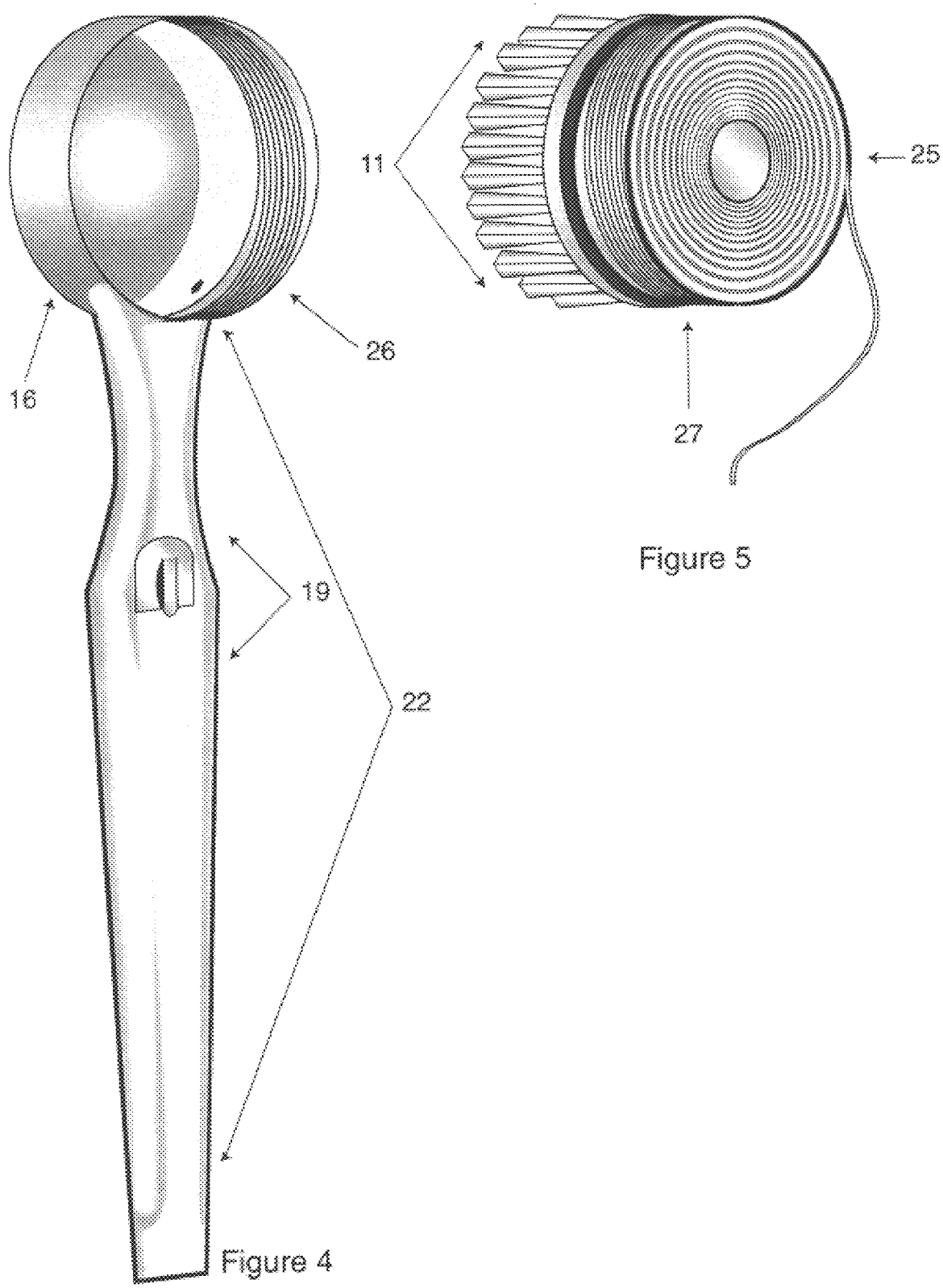
FIG. 4 is a frontal view of the retainable and reusable support handle containing the cutting device. This view further illustrates the housing which receives the detachable and disposable bristle head and affixed floss device.
FIG. 5 is a lateral view of the detachable and disposable bristle head with the affixed floss in position to be looped through the sunken hole referenced in FIG. 1. Further illustrated is the circular pattern of the device and imprinted ridges facilitating the securing of the device into the housing of the support handle as shown in FIGS. 3 and 4.

FIG. 4 shows the device, with the housing unit 16 at the top end of handle 3, which receives the circular bristle head 11 when it is screwed into the housing by the system of ridges 26 which allows for secure fitting.

FIG. 5 shows a lateral view of the detachable and disposable circular bristle head 11 and affixed floss 25 positioned for dispensing, with the encased system of ridges 27, for securing or screwing the device into the housing unit 16, located on the top end of the support handle 19.

What is claimed:

1. A combination detachable and disposable toothbrush bristle head with an attached disposable coiled floss unit containing a quantity of floss for dispensing comprising:

a detachable and disposable circular bristle head with a lateral well having a coiled floss recessed in the well; and a rigid reusable elongated member with a housing unit at top end to affix the circular bristle head and to house the coiled floss device and a sunken hole at rear base of the well for dispensing the floss and a handle end with a metal cutter at its mid-range for cutting the dispensed floss.

\* \* \* \* \*